United States Patent [19]

Yokoyama et al.

[11] Patent Number: 4,586,820
[45] Date of Patent: May 6, 1986

[54] APPARATUS FOR MEASURING ANISOTROPY OF LIGHT EMITTED FROM THE SAMPLE

[75] Inventors: Issei Yokoyama; Kiyoaki Hara, both of Kyoto, Japan

[73] Assignee: Horiba, Ltd., Kyoto, Japan

[21] Appl. No.: 594,482

[22] Filed: Mar. 27, 1984

[30] Foreign Application Priority Data

Mar. 31, 1983 [JP] Japan .................................. 58-58432

[51] Int. Cl.$^4$ ...................... G01J 3/443; G01N 21/64
[52] U.S. Cl. .................................. 356/317; 250/458.1; 356/367
[58] Field of Search ............... 356/317, 364, 367, 318, 356/417; 250/365, 458.1, 459.1, 461.1, 461.2

[56] References Cited

U.S. PATENT DOCUMENTS 4,074,939  2/1978  Rabl ................................. 356/364 X
4,419,583 12/1983  Noeller ............................ 356/318 X

FOREIGN PATENT DOCUMENTS 57-137843  8/1982  Japan .

OTHER PUBLICATIONS

Minami et al., *Japanese Journal of Applied Physics*, vol. 14, Suppl. 14-1, 1975, pp. 39–43.
Kelly et al., *Analytical Chemistry*, vol. 48, No. 6, May 1976, pp. 846–856.
Leskovar et al., *Rev. Sci. Instrum.*, vol. 47, No. 9, Sep. 1976, pp. 1113–1121.
Atkinson, *J. Phys. E., Sci. Instrum.* (G.B.), vol. 10, No. 5, May 1977, pp. 482–484.

Primary Examiner—F. L. Evans
Attorney, Agent, or Firm—Wenderoth, Lind & Ponack

[57] ABSTRACT

An apparatus for measuring anisotropy of light emitted from the sample, in which photodetectors are each disposed by either side of the sample and TACs are connected to the abovesaid apparatus each correspondingly to one photodetector so that a vertical polarized component and a horizontal one of light emitted from the sample can be measured at the same time for enabling analysis operation in a short period of time and measurement in high precision.

2 Claims, 1 Drawing Figure

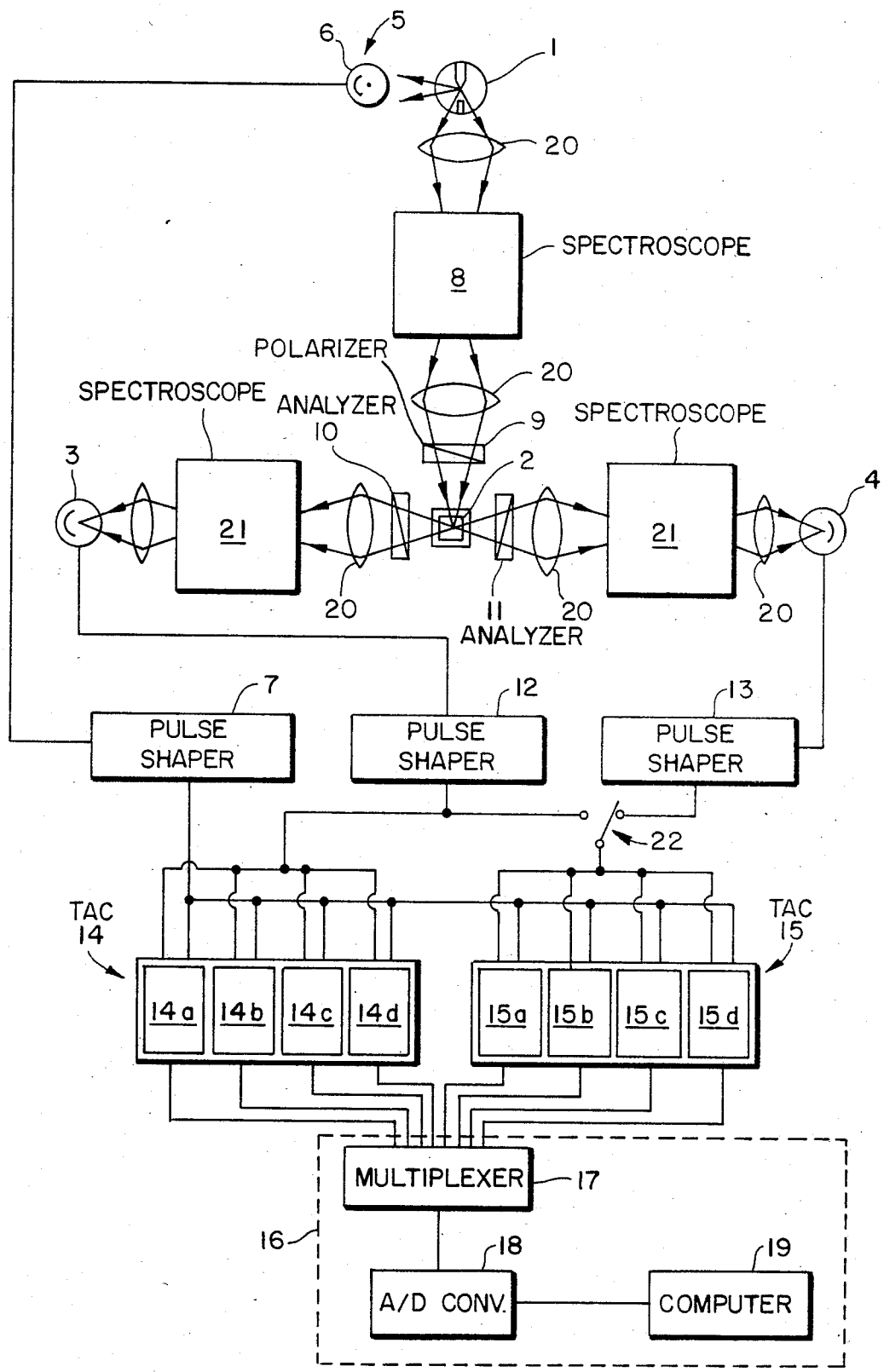

APPARATUS FOR MEASURING ANISOTROPY OF LIGHT EMITTED FROM THE SAMPLE

BACKGROUND OF THE INVENTION

1. Field of the Invention

The present invention relates to an apparatus for measuring anisotropy of light emitted from the sample, in which a vertical component and a horizontal one of polarized light emitted from the sample excited by polarized pulse light are detected for obtaining anisotropy curves from histograms showing the intensity of the abovesaid polarized light components with respect to time. Such kind of apparatus as above are used mainly for analysis of the structure of biochemical substance as high polymer and protein.

2. Description of the Prior Art

In the conventional type anisotropy measuring apparatus, a single light-detecting system is used for detecting a vertical polarized light component and a horizontal one emitted from the sample and, so, requires a long period of time for measurement, thereby being followed by a draw-back that the light intensity of a lamp as a source of pulse light for exciting the sample greatly changes with the lapse of time and measurement results are affected by unavoidable lag between times of measurement of polarized light components.

There is another conventional means in which two light detecting systems, one for detecting the vertical polarized light component and the other for detecting the horizontal one emitted from the sample, are employed and memory in the pulse height analyzer is changed over on the basis of a result of distinguishing one of detecting systems that has detected photons from the other by the use of a memory selector, however, since only one TAC (Time to Amplitude Converter), which is generally featured by its incapability of receiving more than one photopulse as a stop pulse, is used therein, no more than one photopulse can be obtained as data every time of light emission, thereby being attended by a disadvantage that data obtained when both systems detect photopulses cannot but be discarded.

SUMMARY OF THE INVENTION

The present invention, in view of the background as above, is to provide a novel apparatus capable of simultaneously detecting vertical and horizontal components of polarized light emitted from the sample and permitting measurement results to be available as data when both light detecting systems detect photopulses with time lag therebetween or simultaneously every time of light emission.

The gist of the present invention is such that, in an apparatus for measuring anisotropy which detects vertical and horizontal components of polarized light emitted from the sample so as to obtain anisotropy curves from histograms showing the intensity of the abovesaid components with respect to time, there are provided two sets of photodetectors for detecting light emission from the sample, an analyzer allowing a polarized light component parallel with the polarization direction of exciting light projected on the sample to pass therethrough and lying between the photodetector on one side and the sample, and the other analyzer allowing a polarized light component perpendicular to the polarization direction of the abovesaid exciting light projected on the sample to pass therethrough and lying between the other photodetector and the sample, and two sets of TAC which simultaneously start operating at the standard time for projecting exciting light on the sample are individually connected to corresponding photodetectors so that one set of TAC can stop operating separately from the other set by using photopulse as stop pulse generated in each photodetector and simultaneous detection of vertical and horizontal polarized light components can be performed.

BRIEF DESCRIPTION OF THE DRAWINGS

The drawing shows an overall arrangement of an embodiment of the present invention.

DESCRIPTION OF THE PREFERRED EMBODIMENTS

An embodiment of the present invention will be described with reference to the drawing as follows:

In the drawing, the reference numeral 1 indicates a light source to emit pulse exciting light; 2, a sample; 3 and 4, photodetectors, for example, photomultiplier tubes for detecting light emitted from the sample; and 5, a start pulse generating circuit to detect pulse exciting light emitted by the abovesaid light source 1 for pulse excitation and to emit start pulse for starting the operation of TAC, which will be described later, at the standard time for emitting the abovesaid pulse exciting light, the circuit 5 being composed of a photodetector 6 and a pulse shaping circuit 7.

Spectroscopic means 8, such as a spectroscope or a filter, and a polarizer 9 are provided between the abovesaid light source 1 and the sample 2. Between the photodetector 3 and the sample 2, provided is an analyzer 10 for adapting the polarized light component parallel with the polarization direction of the pulse exciting light passing through the abovesaid polarizer 9 and projected on the sample 2 to pass therethrough, and, between the photodetector 4 and the sample 2, another analyzer 11 for adapting the polarized light component perpendicular to the polarization direction of the abovesaid exciting light to pass therethrough is provided. Thus, the light from the sample 2 is separated into a vertical polarized component and a horizontal polarized component by the abovesaid analyzers 10 and 11, each polarized light component being detected by any of separate photodetectors 3 and 4. Reference numerals 12 and 13 denote pulse shaping circuits for shaping photopulses generated in each of the abovesaid detectors 3 and 4.

Reference numerals 14 and 15 indicate two sets of TAC separately connected to photodetectors 3 and 4 through the abovesaid pulse shaping circuits 12 and 13. Two sets of TAC 14 and 15 start operating at the same time when actuated by start pulse generated in the start pulse generating circuit 5, and a set of TAC on one side is stopped by photopulse which is generated by photon detected by a photodetector 3 and serves as stop pulse while the other set of TAC is stopped by photopulse which is generated by photon detected by the other photodetector 4 and serves as stop pulse. The term "TAC" applies to such an apparatus as outputting electric voltage proportional to the lapse of time and functioning on the principle that, in general, charging of the condenser with constant current is started by start pulse and stopped when photopulse is inputted. As apparent from the abovesaid principle, upon detection of charged voltage in the condenser, voltage proportional to the lapse of time between input of start pulse and that of photopulse can be known. Since characteristics of TAC permits counting of no more than one stop pulse, the abovesaid two TACs are each generally composed in multi-channel structure so that a plurality of photopulses emitted in turn by photodetectors 3 and 4 every time of light emission can be counted by TAC in each channel. As has been disclosed in the Japanese Patent, Laid-Open No. 137843/1982, an art of multi-channel structure is known. In the embodiment shown in the drawing, each TAC contains 4 (four) channels denoted as 14a-14d or 15a-15d. The reference numeral 16 represents circuit means for making up histograms, while taking out output voltage of the abovesaid TACs 14 and 15, for showing the intensity of vertical and horizontal polarized light components with respect to time, which is composed of a multiplexer 17, A/D converter 18, and computer 19 for computing voltage in TACs corresponding to respective channels. Assuming histograms of a vertical polarized light component and of a horizontal one as $I_{11(t)}$ and $I_{\perp(t)}$, respectively, an anisotropy curve $\gamma_{(t)}$ can be obtained from the following equation:

$$\gamma_{(t)} = (I_{11(t)} - I_{\perp(t)}) / I_{11(t)} + 2I_{\perp(t)}$$

When correction is required for polarization characteristics, if present in the light detecting system as spectroscope or photomultiplier, an anisotropy curve may be obtained, after $I_{11(t)}$ and $I_{\perp(t)}$ are obtained with respect to both cases that the polarizer 9 is set vertically and horizontally, by the following equation:

$$\gamma(t) = \frac{\left\{1 - \left(\frac{I_{\perp(t)}^V}{I_{11(t)}^V}\right) \cdot \left(\frac{I_{11(t)}^H}{I_{\perp(t)}^V}\right)\right\}}{\left\{1 + 2\left(\frac{I_{\perp(t)}^V}{I_{11(t)}^V}\right)\left(\frac{I_{11(t)}^H}{I_{\perp(t)}^H}\right)\right\}},$$

where: $-I_{11(t)}^V$ and $I_{\perp(t)}^V$ denote histograms of vertical polarized light component and of horizontal one, respectively, obtained when the polarizer 9 is set along the direction of the vertical polarized light component, and $I_{11(t)}^H$ and $I_{\perp(t)}^H$ denote histograms of vertical polarized light component and of horizontal one, respectively, obtained when the polarizer is set along the direction of the horizontal polarized light component. In the drawing, reference numerals 20, 21, and 22 indicate lenses, spectroscopic means, and a changeover switch, respectively. When this switch 22 is turned to the side opposite to that shown in the drawing, photopulses detected by the photodetector 3 on one side can be counted by all TACs 14 and 15, whereby eight photopulses can be counted at the maximum. Such arrangement as above is useful because the multi-channel TAC can efficiently be used for ordinary measurement of fluorescence damping curve in addition to measurement of polarized light components.

As has been described, since an apparatus for measuring anisotropy of light emitted from the sample according to the present invention detects a vertical polarized light component and a horizontal one at the same time by means of two photodetectors and adapts individual TAC to count the number of photopulses of each of polarized light components generated in both photodetectors, the quantity of emitted light required for analysis of anisotropy thereof can be measured at the same time, and, because of a multi-channel provided for each TAC permitting measurement of a number of photoelectric events occurring every time the light is emitted, high effects such as remarkable saving of time for measurement can be exhibited. Further, instability of the light appearing during measurement is reflected on the vertical and the horizontal polarized light components and, as a result, automatically subjected to correction, whereby measurement of anisotropy in high precision is effectively ensured.

We claim:

1. An apparatus for measuring an anisotropy of light emitted from a sample by detecting a vertical polarized component and a horizontal polarized component of light emitted from said sample when said sample is excited by polarized light so as to obtain an anisotropy curves from histograms showing the intensity of said polarized light components with respect to time, said apparatus comprising:

two photodetectors for detecting light emitted from said sample;

an analyzer for allowing a polarized light component parallel with the polarization direction of said exciting polarized light projected on said sample to pass therethrough, said analyzer positioned between one of said photodetectors and said sample;

another analyzer for allowing a polarized light component perpendicular to the polarization direction of said exciting polarized light projected on said sample to pass therethrough, said another analyzer positioned between the other of said two photodetectors and said sample;

two sets of time to amplitude converters which simultaneously start to operate at a standard time when exciting polarized light is projected on said sample, each set of time to amplitude converters being individually connected to corresponding photodetectors;

wherein one set of time to amplitude converters is arranged to stop operating separately from the other set of time to amplitude converters by using a photopulse generated in each photodetector as a stop pulse and wherein simultaneous detection of said vertical and horizontal polarized light components can be performed;

said apparatus further comprising a changeover switch positioned between said two sets of time to amplitude converters and said two photodetectors such that photopulses detected by one of said two photodetectors can be counted by both of said two sets of time to amplitude converters.

2. An apparatus as recited in claim 1, wherein each of said two sets of time to amplitude converters comprise a plurality of channels.

* * * * *